(12) United States Patent
Müller

(10) Patent No.: US 11,051,911 B2
(45) Date of Patent: Jul. 6, 2021

(54) DENTAL APPLICATOR

(71) Applicant: Ivoclar Vivadent AG, Schaan (LI)

(72) Inventor: Frank Müller, Feldkirch (AT)

(73) Assignee: Ivoclar Vivadent AG, Schaan (LI)

(*) Notice: Subject to any disclaimer, the term of this patent is extended or adjusted under 35 U.S.C. 154(b) by 336 days.

(21) Appl. No.: 15/745,154

(22) PCT Filed: Jul. 14, 2016

(86) PCT No.: PCT/EP2016/066768
§ 371 (c)(1),
(2) Date: Jan. 16, 2018

(87) PCT Pub. No.: WO2017/012980
PCT Pub. Date: Jan. 26, 2017

(65) Prior Publication Data
US 2019/0008611 A1    Jan. 10, 2019

(30) Foreign Application Priority Data
Jul. 17, 2015 (EP) ..................................... 15177339

(51) Int. Cl.
*A61C 5/62* (2017.01)
*B05C 17/005* (2006.01)
*A61M 5/34* (2006.01)
*A61M 5/315* (2006.01)

(52) U.S. Cl.
CPC .................. *A61C 5/62* (2017.02); *A61M 5/34* (2013.01); *B05C 17/00593* (2013.01); *A61M 5/31511* (2013.01); *A61M 2005/341* (2013.01)

(58) Field of Classification Search
CPC ......... A61C 5/62; A61M 5/34; A61M 5/3135; A61M 5/3137; A61M 5/31511; A61M 2005/341; A61M 2005/3284; A61M 2005/3286
See application file for complete search history.

(56) References Cited

U.S. PATENT DOCUMENTS

| | | | |
|---|---|---|---|
| 4,776,704 A | * | 10/1988 | Kopunek ............... B01F 5/0615 222/129 |
| 4,863,433 A | | 9/1989 | Payne et al. |
| 5,078,698 A | * | 1/1992 | Stiehl ...................... A61M 5/24 604/235 |

(Continued)

FOREIGN PATENT DOCUMENTS

| CN | 1509773 A | 7/2004 |
|---|---|---|
| FR | 2785813 A1 | 5/2000 |

OTHER PUBLICATIONS

US 5,183,415 A, 02/1993, Fundingsland et al. (withdrawn)

*Primary Examiner* — Yogesh P Patel
(74) *Attorney, Agent, or Firm* — Ann M. Knab; Thad McMurray

(57) ABSTRACT

The invention relates to a dental applicator comprising an applicator housing and a plunger body guided movably in said applicator housing, wherein the applicator housing comprises a connection for detachably mounting a cannula in a pressure-resistant manner, said cannula comprising a connection body and a cannula tube that is rigidly connected in or on said connection body, and the applicator housing (12) and/or plunger body (14) having a receiving device (22) for at least partially receiving a bendable cannula tube (20).

14 Claims, 1 Drawing Sheet

(56) References Cited

U.S. PATENT DOCUMENTS

| | | | |
|---|---|---|---|
| 2004/0064108 A1* | 4/2004 | Krantz | A61M 5/344 604/240 |
| 2007/0016141 A1* | 1/2007 | Salto | A61M 5/3271 604/198 |
| 2011/0151402 A1* | 6/2011 | An | B05C 17/00509 433/82 |
| 2013/0216975 A1 | 8/2013 | Fritze | |

* cited by examiner

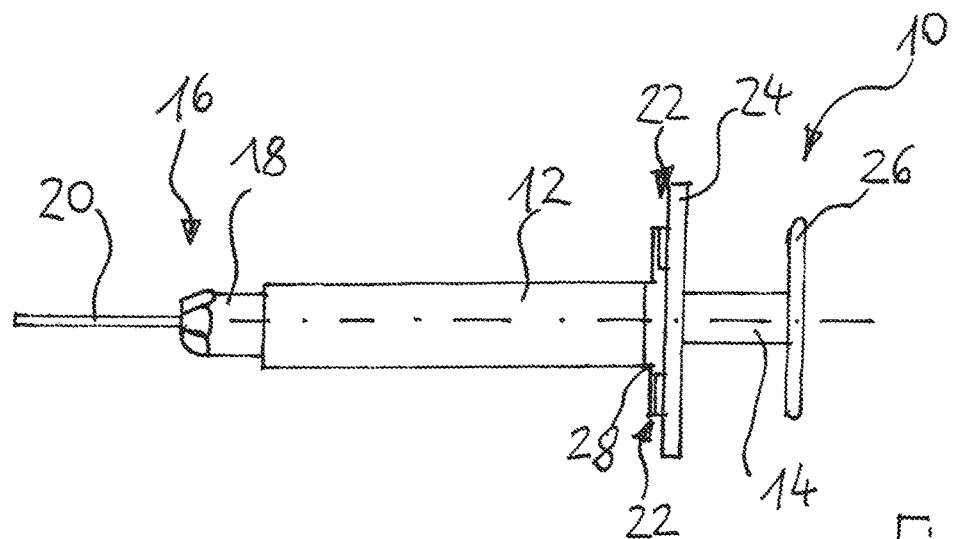
Fig. 1
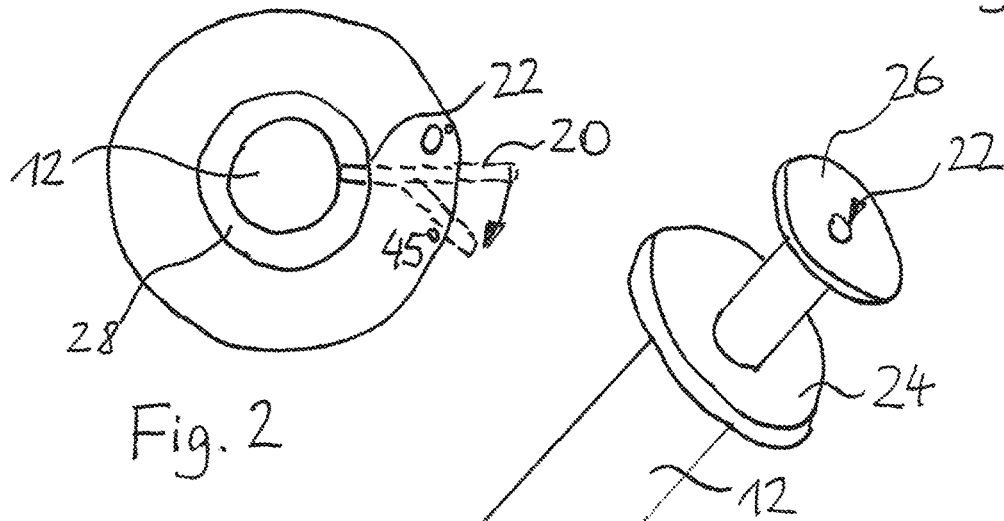
Fig. 2
Fig. 3
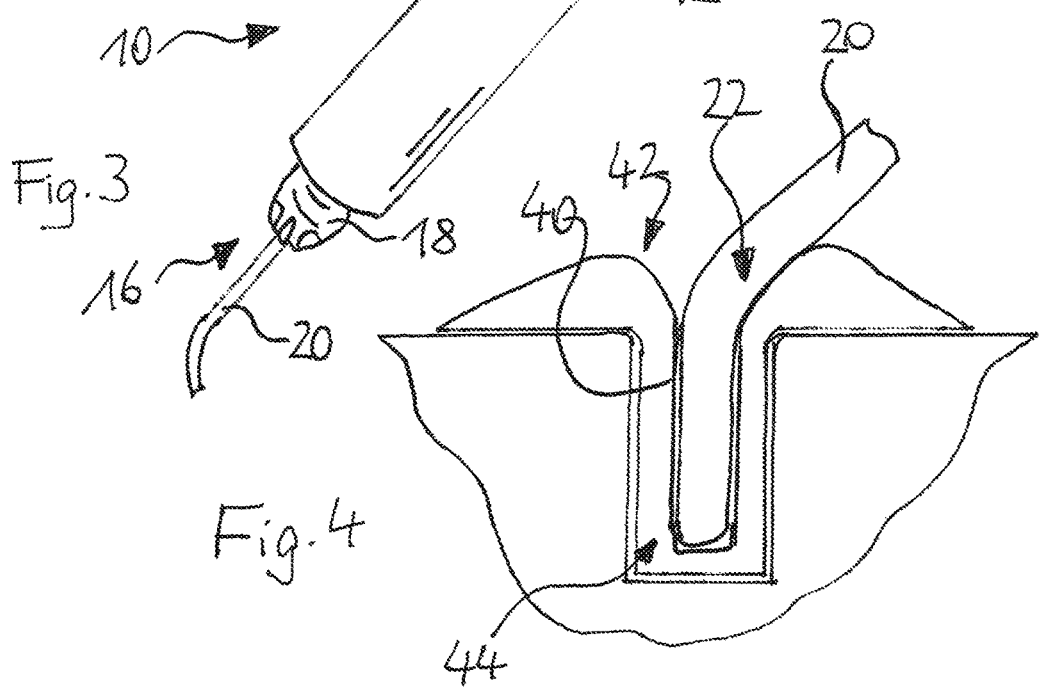
Fig. 4

DENTAL APPLICATOR

CROSS-REFERENCE TO RELATED APPLICATIONS

This application is a National Stage application of International patent application PCT/EP2016/066768 filed on Jul. 14, 2016, which claims priority to European patent application No. 15177339.7. filed on Jul. 17, 2015, the disclosures of which are incorporated herein by reference in their entirety.

FIELD OF THE INVENTION

The invention concerns a dental applicator having an applicator housing and a plunger body guided movably in said applicator housing, and a connection for detachably mounting a cannula in a pressure-resistant manner.

BACKGROUND OF THE INVENTION

It is known that for the application of fluid dental materials, dental applicators are used. Dental materials are often of quite high quality, and the exact metering of the dental material to be applied is therefore necessary not only for dental-medical, but also for economic reasons.

Therefore, dental materials are often held ready in an applicator housing with a plunger, wherein the exact quantity of dental material to be applied is determined with the help of auxiliary devices, such as a scale, for instance.

The dental material frequently needs to be applied in positions which are poorly accessible, such as a root canal of a tooth, for example. For this purpose, a cannula is then typically used, which is provided with a connection body and a cannula tube. The cannula tube has a very small diameter of, for instance, 0.8 mm, wherein the diameter, however, may also vary strongly compared with this.

The cannula is then separable from the applicator housing.

In order to account for the requirements of the application, the producers of such dental applicators offer cannulas with cannula tubes of different designs. Examples for this are straight cannula tubes, but also cannula tubes which have been bent to be curved, which are cranked or which are angled.

In some cases, the dentist now needs to apply the dental material at different places inside the mouth of the patient using the same dental material. So far, he has had to change the cannula with its corresponding cannula tube for this purpose, for instance from straight to angled. In the process, not only a certain amount of dental material was lost, but so far there has been the necessity of keeping ready two different cannulas.

SUMMARY OF THE INVENTION

In contrast to this, the invention is based on the task of creating a dental applicator in accordance with the claims, which is universally usable, i.e. makes possible an adaptation to different application situations, but still makes possible savings from an overall economic point of view.

In accordance with the invention, it is particularly favourable that the applicator housing and/or the plunger body itself, i.e. a part of the dental applicator, makes it possible to adapt the shape of the cannula tube to the different requirements of the application place for the first time.

For this purpose, the cannula tube is provided to be flexible, for instance made out of steel with a wall thickness of 80 µm, with a diameter of 0.8 mm and a total length of 25 mm.

The bending in accordance with the invention is preferably, but not inevitably, done with the help of a bending aid which determines the bending radius. Such a steel tube may be bent without any problem around a bending radius of less than 10 mm, for example of 5 mm.

If the end, i.e., for instance, the foremost 3 mm of the cannula tube, is inserted into the receiving device and a bending force is exerted, this will typically to first result in an elastic, and then a plastic deformation with a bending radius which results essentially uniformly over the course of the tube. Only when the bending radius becomes smaller than admissible, and the tube virtually cracks at some position, a necking is accomplished, and the tube can no longer be used. This, however, is prevented, in accordance with the invention, with the help of the comparatively long cannula tube with a length of at least 10 mm and the comparatively small tube outer diameter with a thickness of 1.5 mm at the most, but also in that, for example, via a stop or the like, the maximum bending is limited.

In accordance with the invention, it is possible for the dentist, with an advantageous embodiment, to adapt the bending shape achieved to the result desired. If the bending radius is to be formed rather close to the connection body, for instance, the dentist will push, during the bending, the applicator housing in the direction towards the receiving aperture, or slightly beyond the receiving device. If, on the other hand, the bending radius is to be created close to the end of the cannula tube, the dentist will slightly pull back the applicator housing during the bending, such that the desired shape will be created in each case.

In this fashion, it is also possible for the bending aid in accordance with the invention to provide an essentially S-shaped course of the cannula tube if this is desired. For this purpose, a pulling force is first exerted during the bending, then the applicator housing is rotated by 180°, and then a pulling force is exerted during the bending.

It is particularly favourable that the receiving device is provided with a depth stop in an advantageous embodiment in accordance with the invention. By means of this, the leverage which is exerted during the bending may be set right from the start. If the depth stop is at a depth of 3 mm, for example, the front 3 mm of the cannula tube will enter into the receiving device, and the length of the bending lever will then also amount to 3 mm, which is sufficient with a diameter of the tube of 1 mm.

It is to be understood that thicker cannula tubes may preferably also be provided with deeper depth stops, and thinner ones with less deep depth stops. A dental applicator may also have a number of receiving devices of different diameters, depending on the cannula applied and its tube.

Preferably, the cannula tube is inserted into the receiving device with its end with little clearance of, for instance, 20 µm or 50 µm. The cannula tube may then be easily detached after the bending, but there is still a secure bending guidance.

In the case that the applicator housing or the plunger housing is produced by injection moulding, the receiving device may be directly integrated in it, for example by means of a corresponding blind hole.

However, it is also possible to produce a corresponding bushing separately out of some suitable material and insert it into a corresponding recess in the applicator housing or in the plunger body. This embodiment is preferable when the same applicator housing and plunger body are to be held ready for different diameters of the cannulas, but afterwards—for instance depending on the material—a decision is to be made for one.

For this purpose, during packing, the corresponding receiving device bushing is then packed together with the applicator housing and the plunger body suiting the cannula.

It is insofar also possible to pack and deliver the receiving device bushing together with a suiting cannula.

Preferably, the cannula tubes in accordance with the invention are straight in their delivered state, and may then be bent into any shape with the help of the receiving device in accordance with the invention.

In an advantageous embodiment, the receiving device is distinctly deeper than it would be required by the actual bending process. A straight portion is followed by a curved portion of a length of several millimetres. The bending is now done in such a fashion that the bending tube leans against the curved portion at some position, and therefore the bending radius is predetermined there. This has the advantage that the radius will by no means become smaller than is minimally admissible.

In an advantageous embodiment it is intended to provide the receiving device at any suitable position of the applicator housing and/or of the plunger body which is provided with a corresponding wall thickness. This has the advantage that no additional protrusion or the like needs to be provided there. A notable weakening of the structure of the plunger body and/or the applicator housing is not connected with this.

In this fashion, the receiving device may, for example, be put into practice without any problem on the back plate or grill plate of the applicator housing essentially radially. Another possibility of attachment is the press plate of the plunger body, wherein here there is the possibility of radial or coaxial positioning.

A number of receiving devices with suitable diameters may also be attached at the suitable position, and it is also possible to put into practice an angle scale in case of radial arrangement to indicate the curvature of the cannula tube.

BRIEF DESCRIPTION OF THE DRAWINGS

Further advantages, details and features result from the following description of several exemplary embodiments of the invention with the help of the drawings which show:

FIG. 1 a schematic side view of an embodiment of a dental applicator in accordance with the invention;

FIG. 2 the embodiment in accordance with FIG. 1, however depicting the applicator housing with the cannula detached, viewing it from underneath;

FIG. 3 a schematic perspective view of a further embodiment of a dental applicator in accordance with the invention; and FIG. 4 a detail of a further embodiment of a dental applicator in accordance with the invention.

DETAILED DESCRIPTION

In FIG. 1, a dental applicator 10 in one embodiment is depicted schematically. The dental applicator is provided with an applicator housing 12 in which a plunger body 14 is guided in a basically known fashion. The guidance may, for instance, be a sliding guide in the manner of a syringe. However, it may also be provided with a threading, such that material may be squeezed out of the applicator housing at great pressure by means of rotating the plunger body.

The dental applicator 10 is further provided with a cannula 16 which is detachably attached to the front end of the applicator housing. The attachment is done, for example, via a screw thread or, for example, a bayonet lock. In a basically known fashion, the attachment is formed such that a sealing is accomplished, such that dental material under pressure, which is provided inside the applicator housing 14, is squeezed into the cannula 16.

The cannula 16 consists of a connection body 18 and a cannula tube 20. The connection body 18 is preferably made out of a plastic material suitable for this purpose, as are the applicator housing 12 and the plunger body 14. In contrast, the cannula tube 20 is flexible in accordance with the invention. The cannula tube 20 is insofar plastically deformable with corresponding bending forces, but may additionally also be elastically deformable to a lower extent.

It is preferably rather thin-walled with a wall thickness of, for example, between 50 μm and 200 μm, and a diameter of, for example, 1 mm. Its length may amount to between 1 cm and, for instance, 3 cm. It may be made out of steel or any other suitable material which, in any case, is resistant to the dental material to be applied.

In accordance with the invention, the dental applicator is provided with a receiving device 22 in the area of the applicator housing/plunger body. In the embodiment depicted, two receiving devices 22 are depicted slightly schematically. They extend in the manner of blind holes parallel to a handle plate 24 of the applicator housing. The handle plate 24 serves for the purpose of closing the applicator housing towards the back and is also a gripping device at the same time. It is typically gripped from behind with two fingers, for example with index finger and middle finger, while pressure is exerted onto a press plate 26, which closes the plunger body 14 towards the back, by the thumb.

The receiving devices 22 extend in a radial direction in the form of blind holes. They are formed on an annular reinforcement 28 which leans against the handle plate 24 in the direction towards the cannula 16 and also serves as a gripping device. The diameter of one receiving device amounts to 1.25 mm and is insofar determined for the receiving of cannula tubes with a diameter of 1.2 mm. In contrast to this, the diameter of the other receiving device amounts to 1.05 mm and is determined for the receiving of cannula tubes with a diameter of 1.0 mm The depth of the receiving device concerned, which is formed in the manner of a blind hole, amounts to 3.5 mm or 3 mm, respectively.

This exemplary embodiment allows a slim configuration of the dental applicator in accordance with the invention. In order to accomplish the bending process, the cannula tube 20 is detached and is inserted into the suiting receiving device 22 and may then be bent as desired.

After the bending process, the cannula 16, with the cannula tube 20 now curved, is again attached, together with the connection body 18, to the applicator housing 12.

From FIG. 2 it can be taken that the handle plate 24 may bear markings which numerically support the bending process. For this purpose, the markings 0°, 30° and 45°, corresponding to one bending around each respective angle named, are entered. The user may thus see, when inserting into the receiving device 22 of the applicator housing 12 or the annular reinforcement 28, respectively, around what angle he is just doing the bending.

In another embodiment which is not depicted here, stops are provided which make it possible to limit the bending process and at the same time suggest to the user from what bending angle on a necking of the cannula tube 20 would have to be feared.

The invention is not limited to the arrangement of the receiving device 22 on the applicator housing 12. The receiving device may be attached at any suitable position, also somewhere on the wall or the front side of the applicator housing 12.

In accordance with FIG. 3, it is attached centrally inside the plunger body 14 within the press plate 26. Here as well it holds true that when the connection body 18 is removed from the applicator housing 12 and the cannula tube 20 is inserted into the receiving device 22 with its front tip, bending is possible. In accordance with FIG. 3, the cannula tube 20 is already provided with a bent tip.

From FIG. 4, the embodiment of a receiving device 22 is visible in detail. Here, the receiving device 22 is provided in the form of a bushing 40, wherein it is to be understood that a corresponding shape is also possible with an integrated, i.e. a one-piece, implementation.

The end 42 of the receiving device 22 which points towards the outside is provided with a radius which at the same time forms a bending stop. The cannula tube 20 may thus be bent along the curved end 42 with a predetermined bending radius. The curved end surface 42 has the shape of a circular ring, such that it may be bent into any direction. An embodiment of the bending end with predetermined ramp angles (43) is also imaginable.

As can be seen from FIG. 4, the receiving device 22 forms at the same time a depth stop 44. The cannula tube 20 may be inserted down to the bottom of the receiving device, which is until the tip of the cannula tube 20 abuts against the bottom of the receiving device inside the receiving device.

In this position, the cannula tube 20 or, to be more precise, its front end, may be bent in any suitable fashion.

In the exemplary embodiment depicted in accordance with FIG. 4, the bushing 40 is exchangeable, such that also bushings with receiving devices 22 with any different suitable inside diameter may be inserted instead of the former.

The invention claimed is:

1. A dental applicator comprising: an applicator housing and a plunger body guided movably in said applicator housing, wherein the applicator housing comprises a connection for detachably mounting a bendable cannula in a pressure-resistant manner, said cannula comprising a connection body and a cannula tube that is rigidly connected in or on said connection body, wherein the applicator housing has a recess for receiving the bendable cannula tube, wherein the recess is a radially extending recess formed as a blind hole on an annular reinforcement member of the applicator housing located proximate an entry of the applicator housing.

2. The dental applicator in accordance with claim 1, wherein the cannula tube is insertable into the radially extending recess.

3. The dental applicator in accordance with claim 1, wherein the recess is provided with a depth stop and wherein the cannula tube is insertable into the recess until the cannula tube abuts against the depth stop.

4. The dental applicator in accordance with claim 1, wherein the recess has a depth which amounts to at least twice a diameter of the cannula tube.

5. The dental applicator in accordance with claim 4, wherein the diameter of the cannula tube provides a clearance of at least 50 µm inside the recess, and wherein the recess has an inside diameter which is at least 50 µm larger than the circumference of the cannula tube.

6. The dental applicator in accordance with claim 1, wherein the recess is provided with at least two bending stops which are spaced apart from each other, which bending stops are offset towards each other by 180°.

7. The dental applicator in accordance with claim 1, wherein the recess is circular and has a straight course.

8. The dental applicator in accordance with claim 1, wherein the recess is provided, on an outward-pointing end, with at least one curved end surface which extends in a circularly curved fashion around the outward-pointing end.

9. The dental applicator in accordance with claim 8, wherein the curved end surface is provided with a radius which corresponds to at least the minimally admissible bending radius of the cannula tube.

10. The dental applicator in accordance with claim 8, wherein the curved end surface is provided on the levelling-off margin of the radius, with at least one pre-defined ramp angle.

11. The dental applicator in accordance with claim 1 wherein the recess enters into the plunger body in a fashion coaxially with the plunger body.

12. The dental applicator in accordance with claim 1, wherein the recess extends radially away from a shank of the plunger body or from the applicator housing, adjacently to the respectively associated handle plate, and wherein on the handle plate which is adjacent to the recess, angle markings are attached which signal the bending angle of the cannula tube during the bending of the end of the cannula tube which is inserted into the recess.

13. The dental applicator in accordance with claim 1, wherein the recess has a depth which is at least three times a diameter of the cannula tube.

14. The dental applicator in accordance with claim 1, wherein the recess has a depth which is no more than ten times a diameter of the cannula tube.

* * * * *